(12) United States Patent
Yu et al.

(10) Patent No.: US 10,067,110 B2
(45) Date of Patent: Sep. 4, 2018

(54) ADULTERATED PEANUT OIL DETECTOR AND ADULTERATED PEANUT OIL DETECTION METHOD

(71) Applicant: CHANGCHUN JILIN UNIVERSITY LITTLE SWAN INSTRUMENTS CO., LTD, Changchun (CN)

(72) Inventors: Aimin Yu, Changchun (CN); Zhende Wang, Changchun (CN)

(73) Assignee: CHANGCHUN JILIN UNIVERSITY LITTLE SWAN INSTRUMENTS CO., LTD, Changchun (CN)

(*) Notice: Subject to any disclaimer, the term of this patent is extended or adjusted under 35 U.S.C. 154(b) by 238 days.

(21) Appl. No.: 15/228,350

(22) Filed: Aug. 4, 2016

(65) Prior Publication Data

US 2017/0030878 A1 Feb. 2, 2017

Related U.S. Application Data

(62) Division of application No. 13/056,891, filed as application No. PCT/CN2009/001395 on Dec. 9, 2009.

(30) Foreign Application Priority Data

Feb. 18, 2009 (CN) .......................... 2009 1 0077338

(51) Int. Cl.
*G01N 33/00* (2006.01)
*G01N 33/03* (2006.01)
(Continued)

(52) U.S. Cl.
CPC .............. *G01N 33/03* (2013.01); *G01N 1/28* (2013.01); *G01N 21/27* (2013.01); *G01J 3/28* (2013.01);
(Continued)

(58) Field of Classification Search
CPC .................................. G01N 33/03; G01J 3/28
See application file for complete search history.

(56) References Cited

U.S. PATENT DOCUMENTS

| 8,209,128 | B1 | 6/2012 | Gourley |
| 2007/0189925 | A1 | 8/2007 | Blecka et al. |

(Continued)

FOREIGN PATENT DOCUMENTS

CN           101482494 B        5/2011

*Primary Examiner* — Tri Ton
*Assistant Examiner* — Rebecca C Bryant
(74) *Attorney, Agent, or Firm* — Scully Scott Murphy & Presser

(57) ABSTRACT

The present invention provides an adulterated peanut oil detector and an adulterated peanut oil detection method, and pertains to the technical domain of product analysis. The detector comprises a casing, a LCD and Return key, Enter key, Up key, Down key, a power switch, a power socket, and a USB interface arranged on the casing, and a microprocessor and a power supply unit mounted in the casing and electrically connected to the components on the casing, wherein, a module cover is arranged on the top surface of the casing, and a pretreatment module and a detection module are mounted in the space under the module cover. The pretreatment module comprises a heating body and cuvette slots, and the detection module comprises an axial fan, a radiating plate, a refrigerating plate, and cuvette slots. The detection method comprises sample preheating procedure and slow refrigeration procedure. The detector and method provided in the present invention can quickly and easily detect whether the peanut oil sample is adulterated and the percentage of adulteration, and is applicable to quick on-spot detection of rapeseed oil, sunflower oil, maize oil, cotton oil, palm oil, and soybean oil, etc. admixed in peanut oil.

10 Claims, 3 Drawing Sheets

(51) Int. Cl.
  *G01N 1/28* (2006.01)
  *G01N 21/27* (2006.01)
  *G01J 3/28* (2006.01)
  *G01N 21/17* (2006.01)

(52) U.S. Cl.
  CPC ............... *G01N 2021/1748* (2013.01); *G01N 2201/062* (2013.01); *G01N 2201/13* (2013.01)

(56) References Cited

U.S. PATENT DOCUMENTS

| | | |
|---|---|---|
| 2008/0014118 A1 | 1/2008 | Kitagawa et al. |
| 2012/0290219 A1 | 11/2012 | Stark et al. |

ADULTERATED PEANUT OIL DETECTOR AND ADULTERATED PEANUT OIL DETECTION METHOD

CROSS-REFERENCE TO RELATED APPLICATION

This application is a divisional application of co-pending U.S. application Ser. No. 13/056,891, filed Jan. 31, 2011, which is a 371 national phase application of International Application No. PCT/CN2009/001395, filed Dec. 9, 2009, which claims priority from Chinese Application No. 200910077338.6, filed Feb. 18, 2009, the entire contents of which are incorporated herein by reference.

FIELD OF THE TECHNOLOGY

The present invention pertains to the technical domain of product analysis, and relates to an easy-to-use, sensitive, and quick on-spot adulterated peanut oil detector, in particular to an analytical apparatus and a detection method for quickly detecting rapeseed oil, sunflower oil, maize oil, cotton oil, palm oil, and soybean oil adulterated in peanut oil on the spot.

BACKGROUND TECHNOLOGY

Peanut oil is famous for its rich nutrients, and is one of edible oil products sold at the highest price among edible oil products in the market. Under normal conditions, peanut oil is in light-yellow, transparent, and clear color and luster, with aromatic smell and delicious taste, and is an edible oil product easy to digest. Peanut oil contains unsaturated fatty acids at 80% or higher percentage (including 41.2% oleic acid and 37.6% linoleic acid). In addition, peanut oil contains saturated fatty acids such as palmic acid, stearic acid, and arachidic acid. Moreover, peanut oil contains substances beneficial for human body, such as sterol, maltol, phosphatide, vitamin E, and choline, etc. It is seen from above data that the fatty acids in peanut oil are easy to digest and absorb by human body. Reports in foreign countries state that eating peanut oil regularly not only is helpful for decomposing cholesterol in human body into bile acids and excreting the bile acids out of human body, but also can reduce the content of cholesterol in blood. In addition, eating peanut oil regularly can prevent skin cracking and aging, protect blood vessel wall, prevent thrombosis, and is helpful for preventing arteriosclerosis and coronary heart diseases. The choline in peanut oil can improve brain retentivity and postpone brain function declination. It is seen that peanut oil is an edible oil product highly beneficial for human health. However, driven by interest pursuing, peanut oil adulteration activities remain incessant after repeated prohibition.

The high price difference between peanut oil and rapeseed oil/palm oil/soybean oil (at present, in the market in Guangzhou, China, the price of peanut oil is approx. RMB10,250/t, while the price of soybean oil is RMB5,400/t, the price of rapeseed oil is RMB6,150/t, and the price of palm oil is RMB4,380/t) provides an opportunity to unscrupulous vendors. These vendors or individuals adulterate other vegetable oils in peanut oil, or even replace peanut oil with other vegetable oils completely, with a small amount of peanut oil essence mixed for flavor treating. However, such adulterate peanut oil is usually hard to distinguish solely by means of smelling or refrigeration. Therefore, it is highly necessary to develop a detector that can distinguish adulterated peanut oil.

SUMMARY OF THE INVENTION

In view of above problem, the present invention provides a quick analyzer that can distinguish adulterated peanut oil simply and quickly on the spot.

To attain above object, the adulterated peanut oil detector provided in the present invention comprises a casing, a LCD and Return key, Enter key, Up key, Down key, a power switch, a power socket, and a USB interface arranged on the casing, a microprocessor and a power supply unit mounted in the casing and electrically connected to the components on the casing; a module cover is arranged on the top surface of the casing, and a pretreatment module and a detection module are mounted in the space below the module cover.

In the adulterated peanut oil detector, the pretreatment module comprises a main body and a heating body attached to the bottom of the main body; the main body has two upward-opening cuvette slots and a temperature sensor mounted on one side; both the heating body and the temperature sensor are electrically connected with the microprocessor and the power supply unit.

From top to bottom, the detection module comprises an axial fan, a radiating plate, a refrigerating plate, and a main body of detection module, with a temperature sensor arranged on the main body of detection module; in the main body of detection module, two upward-opening cuvette slots are arranged vertically, two through holes intersecting with the cuvette slots are arranged horizontally, light source/monochromators are mounted in one end of the through holes, and photoelectric detectors are mounted in the other end of the through holes; in the detection module, the axial fan, radiating plate, refrigerating plate, temperature sensors, light sources/monochromators, and photoelectric detectors are electrically connected with the power supply unit and the microprocessor.

Vent holes are arranged on the bottom of the casing.

A printer is mounted in the casing, with an exit slot arranged on the top surface of the casing; the printer is electrically connected with the power supply unit and the microprocessor.

Another object of the present invention is to provide an adulterated peanut oil detection method.

The method utilizes the adulterated peanut oil detector described above, and comprises the following steps: first, the cuvette containing the sample to be detected is loaded into the pretreatment module and heated for 10 min. at 40° C. constant temperature; then, the cuvette containing the sample is taken out and loaded into the detection module kept at 3-4° C. constant temperature for testing for 25 min.; in the detection process, the detection signals are processed by the microprocessor to create a detection curve, which is compared by the microprocessor with the standard curves in a standard curve library, to output the detection result.

In the detection method, the standard curves include standard curve of quality peanut oil and standard curves of peanut oils adulterated with other oils at different percentages of adulteration.

The detection result is the percentage of adulteration that indicates whether the tested sample is quality peanut oil or adulterated peanut oil. The detection result is outputted on the LCD, through the USB interface, or on the printer.

The technical scheme described above in the present invention has the following advantages:

1. The present invention employs an approach of comparison with standard curves in a standard curve library, and therefore is easy to operate, and provides intuitive detection result.

2. The present invention is in a modular structure, resulting in improved performance stability.
3. The present invention employs microprocessor-based control, and has measurement, setting, recording, storage, and data processing functions. It has a USB interface, and can communicate with a PC. The present invention achieves a high degree of automation.
4. The present invention has a large LCD and a Chinese user interface, supports man-machine interaction, and is compact in size, light in weight, and easy to use.

The present invention can detect the quality of peanut oil product quickly. It can detect rapeseed oil, sunflower oil, maize oil, cotton oil, palm oil, and soybean oil, etc. adulterated in peanut oil quickly on the spot.

DETAILED DESCRIPTION OF THE EMBODIMENTS

Hereunder the embodiments of the present invention will be described, with reference to the accompanying drawings.

The adulterated peanut oil detector and method disclosed in the present invention is an analytical apparatus designed on the basis of the fact that the light transmittance (i.e., absorbance) in the peanut oil sample is different to that in the edible oil to be admixed into the peanut oil because of the difference in solidification temperature between them.

Figure 1:
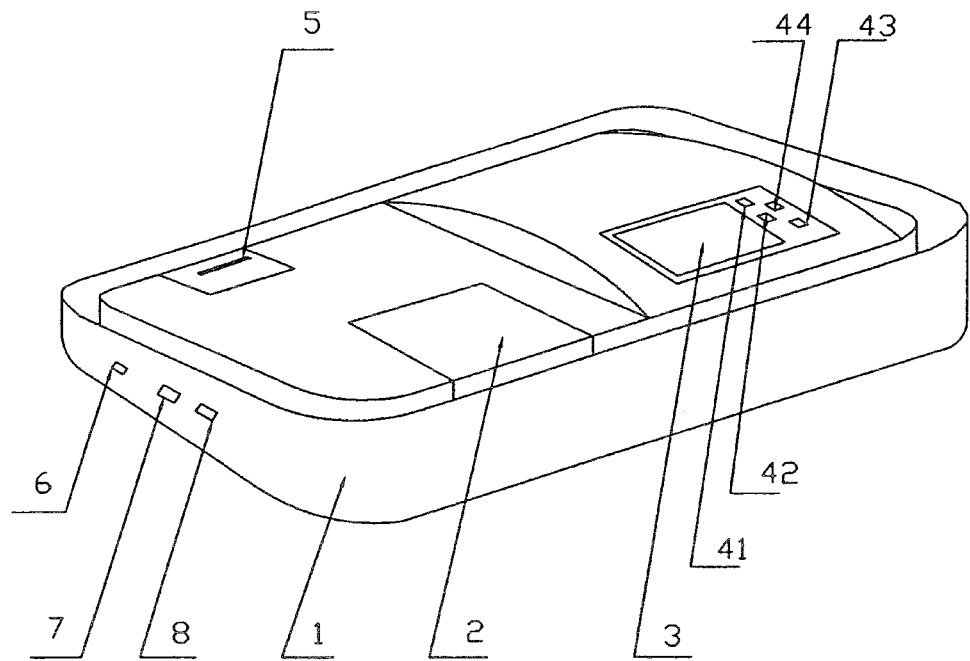
FIG. 1 is a schematic diagram of exterior structure of the main unit of adulterated peanut oil detector provided in the present invention.

As shown in FIG. 1, the adulterated peanut oil detector provided in the present invention comprises a casing 1, and a LCD 3, Return key 41, Enter key 42, Up key 43, and Down key 44 on the top surface of the casing 1. A module cover 2 and a printer exit slot 5 are arranged on the top surface of the casing 1, a power switch 6, a power socket 7, and a USB interface 8 are arranged on the sides of the casing 1, and vent holes (not shown) are arranged on the bottom of the casing 1. A microprocessor, a printer, and a power supply unit are mounted in the space in the casing 1 (see FIG. 4); wherein, a pretreatment module 20 and a detection module 30 are mounted in the space under the module cover 2.

Figure 2:
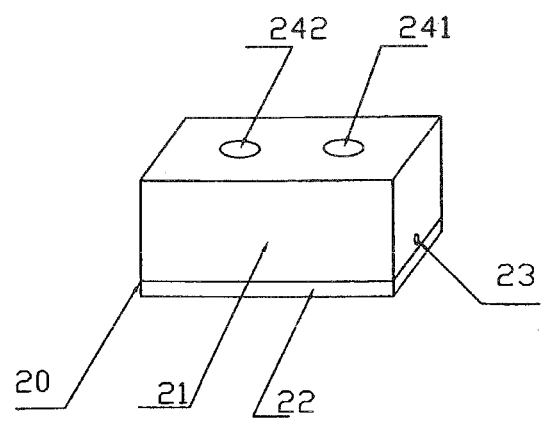
FIG. 2 is a schematic structural diagram of the pretreatment module in the present invention.

As shown in FIG. 2, the main body 21 of the pretreatment module 20 is made of aluminum material, with a PTC heating body 22 attached to the bottom of the main body 21 and a temperature sensor 23 (model 18B20) mounted on one side of the main body 21; the heating body and temperature sensor can be any other heating body and temperature sensor with equivalent efficacy, and no specific limitation is applied to them here; both the heating body 22 and the temperature sensor 23 are electrically connected with the microprocessor and the power supply unit. Two upward-opening cuvette slots 241 and 242 are arranged on the main body 20, and the dimensions and shapes of the slots 241 and 242 match the cuvettes used in detection. When the pretreatment module 20 operates, the main body 21 is heated by the heating body 22, and the temperature of the main body 21 is transmitted by the temperature sensor 23 to the microprocessor, so that the temperature of the main body 21 is controlled at 40° C. by the microprocessor.

Figure 3:
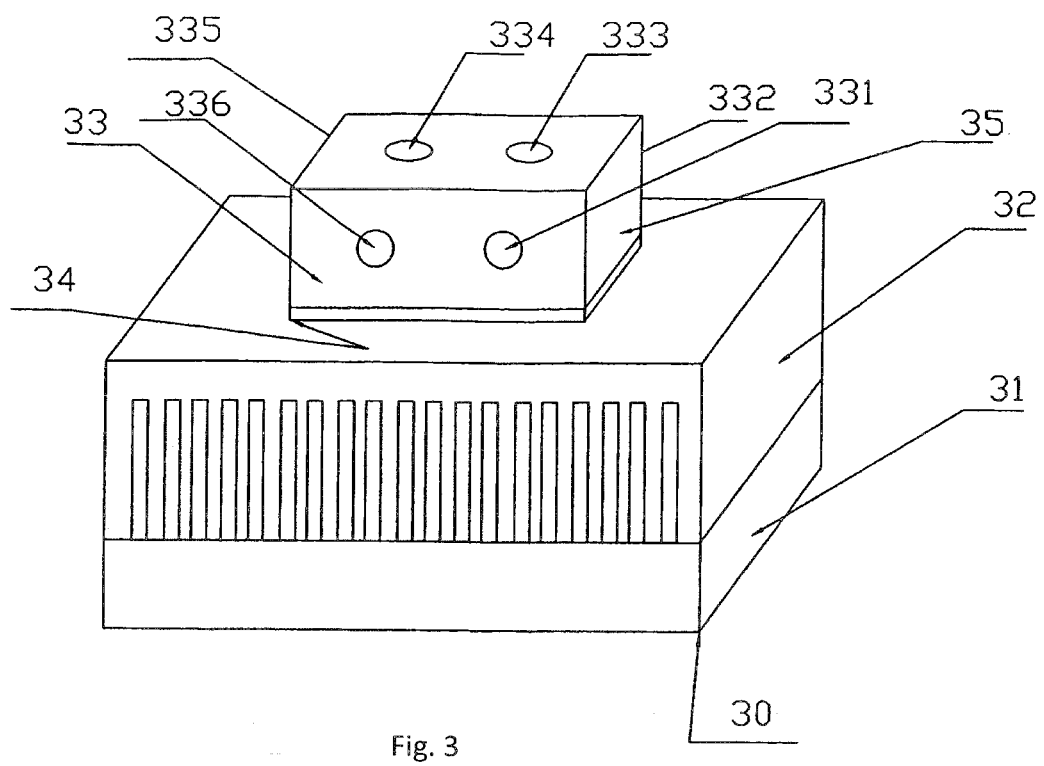
FIG. 3 is a schematic structural diagram of the detection module in the present invention.
Figure 3A:
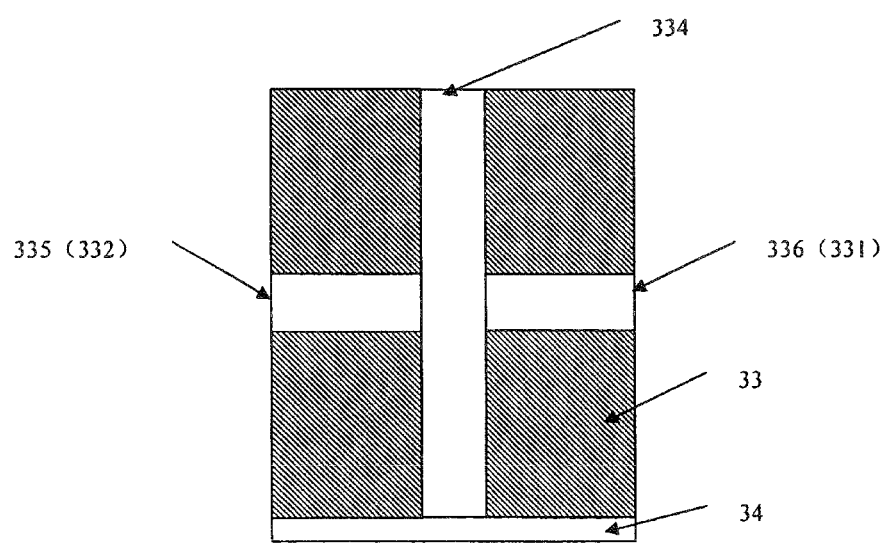
FIG. 3A is a left-viewed sectional diagram of the main structure of the detection module shown in FIG. 3.

As shown in FIG. 3, from top to bottom, the detection module 30 comprises an axial fan 31, a radiating plate 32, a refrigerating plate 34, and a main body 33 made of aluminum material, with a temperature sensor 35 (model 18B20) arranged on the main body 33 of detection module; in the present invention, the temperature sensors, refrigerating plate, radiating plate, and axial fan are general products, and no specific limitation is set on them here, as long as they can work together to achieve required service performance. In the main body 33 of detection module, two upward-opening cuvette slots 333 and 334 are arranged vertically, in size and shape matching the cuvettes used in detection; as shown in FIG. 3A, in the main body 33 of detection module, two through holes intersecting with the cuvette slots 333 and 334 are arranged horizontally, light source/monochromators 332 and 335 are mounted in one end of the through holes, and photoelectric detectors 336 and 331 are mounted in the other end of the through holes. In the detection module 30, the axial fan 31, radiating plate 32, refrigerating plate 34, temperature sensor 35, light source/monochromators 332 and 335, and photoelectric detectors 336 and 331 are electrically connected with the power supply unit 35 and the microprocessor.

When the detection module 30 operates, the refrigerating plate begins to refrigerate, and the heat generated by the refrigerating plate is transferred to the radiating plate 32 and dissipated by the axial fan 31; the temperature of the main body 33 of detection module is transmitted by the temperature sensor 35 to the microprocessor, so that the temperature of the main body 33 of detection module is controlled at 3-4° C. by the microprocessor. During detection, the light source/monochromators 332 and 335 serve as light sources of the analytical apparatus, the light passes through the cuvettes to the photoelectric detectors 336 and 331, and the photoelectric detectors convert the optical signals received from the light source/monochromators into electric signals and transmit the electric signals to the microprocessor.

Figure 4:
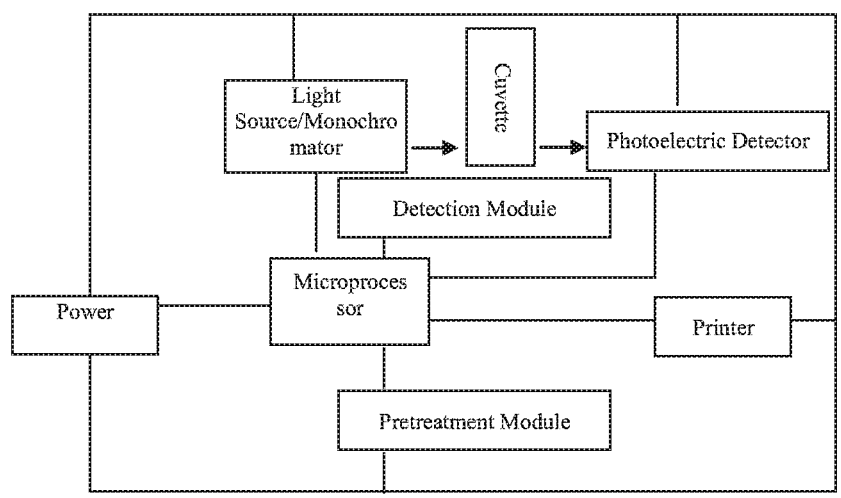
FIG. 4 is a schematic diagram of circuit connections, light paths, and working principle of the working components in the present invention.

FIG. 4 illustrates the circuit connections, light paths, and working principle of the working parts of the present invention: after the apparatus is powered on, the samples are loaded into the cuvettes, the cuvettes are mounted into the cuvette slots of the pretreatment module, the microprocessor controls the pretreatment module to heat up to keep the sample at 40° C. constant temperature (by means of the heating body and temperature sensor); then, the cuvettes containing the samples are loaded into the cuvette slots of the detection module, the microprocessor controls the temperature of the main body of detection module to keep the samples at 3-4° C. (by means of the axial fan, radiating plate, refrigerating plate, and temperature sensor); during the detection, the monochromatic light emitted by the light source/monochromators pass through the samples in the cuvettes in the main body of detection module to the photoelectric detectors, the photoelectric detectors convert the detected optical signals into electric signals and transmit the electric signals to the microprocessor, and the microprocessor carries out data analysis and outputs the result on the screen or to the printer.

In the present invention, the light source/monochromator is composed of high-flux LEDs and serves as light source and monochromator. In the embodiments, high-flux LEDs produced by Nichia (Japan) and Toyota (Japan), with luminance higher than 1000 mcd, are employed for the light source/monochromators. The wavelengths are 420 nm. The light source/monochromators are powered continuously or in pulse. The circuit is an ordinary circuit, and will not be further detailed here.

Integrated photoelectric sensors (model TSL230) produced by TI (USA) are employed for the photoelectric detectors. Of course, other equivalent integrated photoelectric sensors can be used in this utility model.

The microprocessor is an ARM Series microprocessor produced by PHILIPS, which is a 32-bit single-chip microprocessor, with 40K internal memory, loaded with general spectrophotometric analysis software. The microprocessor is mainly used to receive output signals from the photoelectric detector and carry out data processing. The circuit connections and working process of a spectrophotometric analyzer composed of light source/monochromators, photoelectric detectors, and microprocessor are described in the applicant's patent application ZL200620004295.0, and will not be further detailed here.

Hereunder the adulterated peanut oil detection method that utilizes the adulterated peanut oil detector in the present invention will be further detailed in an example of application.

Figure 5:
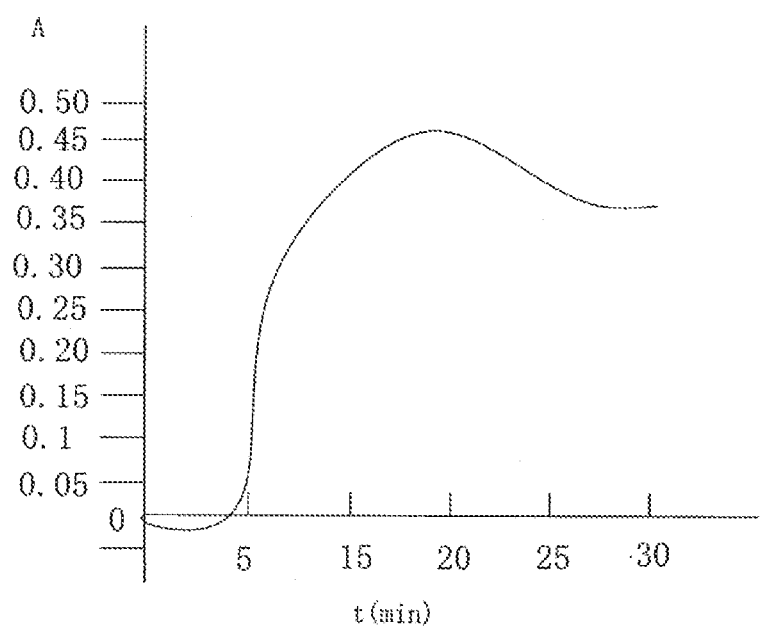
FIG. 5 is a standard curve of quality peanut oil created by the microprocessor in photometric analysis in the present invention.

First, a cuvette containing the sample to be detected is loaded into the pretreatment module and heated for 10 min. at 40° C. constant temperature, in order to ensure sample homogeneity. Then, the cuvette containing the sample to be detected is taken out and loaded into the detection module and detected at 3-4° C. constant temperature for 25 min. In the detection process, as the temperature changes, the degree of solidification of the sample will change, and therefore the light absorbance will change; the photoelectric detector transmits the detection signals continuously to the microprocessor, to generate a detection curve (absorbance-time curve), which is compared with the standard curve of quality peanut oil (see FIG. 5) and curves of peanut oils adulterated with other oils at different percentages, so as to judge whether the peanut oil sample is genuine and determine the percentage of adulteration (if the peanut oil sample is not genuine); then, the detection result is outputted on the display screen, to the printer, or through the USB interface. The data acquisition and processing process is accomplished automatically by the microprocessor.

INDUSTRIAL APPLICABILITY

The adulterated peanut oil detector provided in the present invention is compact in structure, can quickly determine the quality of peanut oil products and detect any rapeseed oil, sunflower oil, maize oil, cotton oil, palm oil, or soybean oil admixed in the peanut oil on the spot, and is suitable for industrial application.

The invention claimed is:

1. An adulterated peanut oil detection method utilizing a detector based on spectrophotometry, comprising the following steps:

pretreating the peanut oil sample by heating at a first constant temperature of 40° C. for a first time period of 10 minutes;

placing the peanut oil sample at a second constant temperature of 3-4° C. for a second time period of 25 minutes;

during the second time period, obtaining a detection curve of absorbance versus time for the peanut oil sample; and comparing the detection curve with standard curves to generate a detection result.

2. The adulterated peanut oil detection method according to claim 1, wherein the standard curves include a standard curve for genuine peanut oil and standard curves for the adulterated peanut oil at various proportions of adulteration.

3. The adulterated peanut oil detection method according to claim 2, wherein the detection result is whether the peanut oil sample to be detected is adulterated peanut oil and/or the proportion of adulteration for the adulterated peanut oil.

4. The adulterated peanut oil detection method according to claim 3, wherein the detector based on spectrophotometry comprises a pretreatment module for pretreatment of the peanut oil sample to be detected and a detecting module for detection of the peanut oil sample to be detected.

5. The adulterated peanut oil detection method according to claim 4, wherein the detecting module comprises:

a first main body having two upwardly-opening first slots for cuvette arranged vertically, and two through holes arranged horizontally intersecting with the first slots for cuvette; and a first temperature sensor attached to the first main body.

6. The adulterated peanut oil detection method according to claim 5, wherein monochromators are mounted as light sources to one end of each through hole, and photoelectric detectors are mounted to the other end of each through hole, such that the incident light path and the exit light path are aligned substantially along the same line.

7. The adulterated peanut oil detection method according to claim 6, wherein the monochromators are high-flux LEDs and the photoelectric detectors are integrated photoelectric sensors.

8. The adulterated peanut oil detection method according to claim 4, wherein the pretreatment module comprises:

a second main body having arranged thereon two upwardly-opening second slots for cuvette and a second temperature sensor mounted on a side thereof; and a heating body attached to the bottom of the second main body.

9. The adulterated peanut oil detection method according to claim 1, wherein the detection result is output through at least one of an LCD, a USB interface and a printer provided on the detector based on spectrophotometry.

10. The adulterated peanut oil detection method according to claim 5, wherein the pretreatment module comprises:

a second main body having arranged thereon two upwardly-opening second slots for cuvette and a second temperature sensor mounted on a side thereof; and a heating body attached to the bottom of the second main body.

* * * * *